(12) United States Patent
Köppel

(10) Patent No.: US 12,220,519 B2
(45) Date of Patent: Feb. 11, 2025

(54) LIQUID MANAGEMENT IN AN OPHTHALMOLOGICAL DEVICE

(71) Applicant: THIS AG, Heerbrugg (CH)

(72) Inventor: Thomas Köppel, Widnau (CH)

(73) Assignee: THIS AG, Heerbrugg (CH)

( * ) Notice: Subject to any disclaimer, the term of this patent is extended or adjusted under 35 U.S.C. 154(b) by 1303 days.

(21) Appl. No.: 16/347,531

(22) PCT Filed: Nov. 2, 2017

(86) PCT No.: PCT/EP2017/078064
§ 371 (c)(1),
(2) Date: May 3, 2019

(87) PCT Pub. No.: WO2018/083179
PCT Pub. Date: May 11, 2018

(65) Prior Publication Data
US 2021/0290836 A1    Sep. 23, 2021

(30) Foreign Application Priority Data
Nov. 3, 2016 (EP) .................... 16197046

(51) Int. Cl.
*A61M 1/00* (2006.01)

(52) U.S. Cl.
CPC .............. *A61M 1/72* (2021.05); *A61M 1/64* (2021.05); *A61M 1/77* (2021.05); *A61M 1/772* (2021.05); *A61M 2205/12* (2013.01); *A61M 2205/332* (2013.01); *A61M 2205/3337* (2013.01); *A61M 2210/0612* (2013.01)

(58) Field of Classification Search
CPC .......... A61M 1/72; A61M 1/77; A61M 1/772; A61M 1/64; A61M 2205/12; A61M 2205/332; A61M 2205/3337; A61M 2210/0612
USPC ....................................... 604/294
See application file for complete search history.

(56) References Cited

U.S. PATENT DOCUMENTS

| 5,163,900 A | 11/1992 | Wortrich |
| 5,282,787 A | 2/1994 | Wortrich |
| 5,582,601 A | 12/1996 | Wortrich |

(Continued)

FOREIGN PATENT DOCUMENTS

| DE | 69309757 T2 | 8/1997 |
| DE | 69321264 T2 | 2/1999 |

(Continued)

OTHER PUBLICATIONS

International Search Report and Written Opinion dated Jan. 15, 2018 in International Application No. PCT/EP2017/078064.

*Primary Examiner* — Andrew J Mensh
(74) *Attorney, Agent, or Firm* — Muncy, Geissler, Olds & Lowe, P.C.

(57) ABSTRACT

The invention relates to an ophthalmological device (99) which provides suction flushing, having an aspiration function and an infusion function, as well as a replaceable cassette (1) for such a device. It comprises an aspiration conveyor device (52) for motor-driven discharge of liquid from a surgical instrument (29) into a waste container (56). According to the invention, it also comprises an infusion conveyor device (36) for motor-driven supply of an infusion medium from an infusion container (30) to said surgical instrument (29).

11 Claims, 5 Drawing Sheets

(56) References Cited

U.S. PATENT DOCUMENTS

| | | | |
|---|---|---|---|
| 5,800,396 A | 9/1998 | Fanney | |
| 5,897,524 A | 4/1999 | Wortrich | |
| 5,899,674 A | 5/1999 | Jung | |
| 6,283,937 B1* | 9/2001 | Takamatsu | A61M 1/74 604/31 |
| 2007/0104616 A1* | 5/2007 | Keenan | A61B 5/153 422/400 |
| 2008/0114291 A1* | 5/2008 | Muri | A61M 3/0201 604/35 |
| 2010/0286651 A1* | 11/2010 | Sorensen | A61M 1/82 604/151 |
| 2011/0054385 A1 | 3/2011 | Eichler | |
| 2011/0106004 A1* | 5/2011 | Eubanks | A61M 25/0021 604/35 |
| 2011/0313343 A1* | 12/2011 | Milutinovic | A61M 1/74 604/28 |
| 2012/0215160 A1* | 8/2012 | Valenti | A61M 1/74 604/66 |
| 2013/0138035 A1* | 5/2013 | Huculak | A61F 9/00821 604/28 |
| 2013/0245543 A1* | 9/2013 | Gerg | A61M 3/022 604/30 |
| 2014/0163455 A1 | 6/2014 | Wilson | |
| 2014/0323953 A1* | 10/2014 | Sorensen | A61F 9/00763 604/35 |
| 2014/0328697 A1 | 11/2014 | Sorensen | |
| 2016/0045367 A1 | 2/2016 | Horvath | |
| 2020/0054802 A1* | 2/2020 | Köppel | A61M 1/80 |

FOREIGN PATENT DOCUMENTS

| | | |
|---|---|---|
| DE | 69615507 T2 | 5/2002 |
| DE | 69615633 T2 | 7/2002 |
| DE | 69709192 T2 | 8/2002 |
| DE | 69621562 T2 | 1/2003 |
| EP | 3318226 A1 | 5/2018 |
| EP | 3318290 A1 | 5/2018 |
| JP | H07507461 A | 8/1995 |
| JP | 2014507972 A | 4/2014 |
| WO | 1987001943 A1 | 4/1987 |
| WO | 1993024082 A1 | 9/1993 |
| WO | 2002056850 A1 | 7/2002 |
| WO | 2004108189 A2 | 12/2004 |
| WO | 2004110524 A2 | 12/2004 |

* cited by examiner

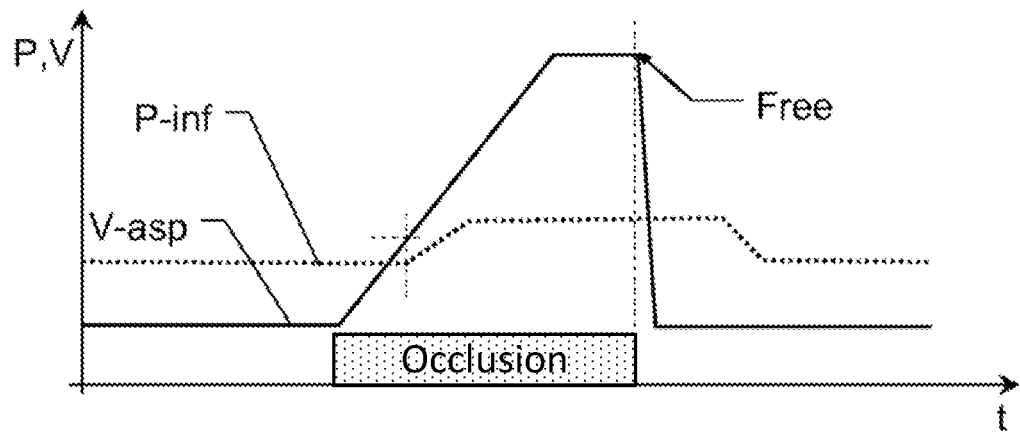
Fig. 9
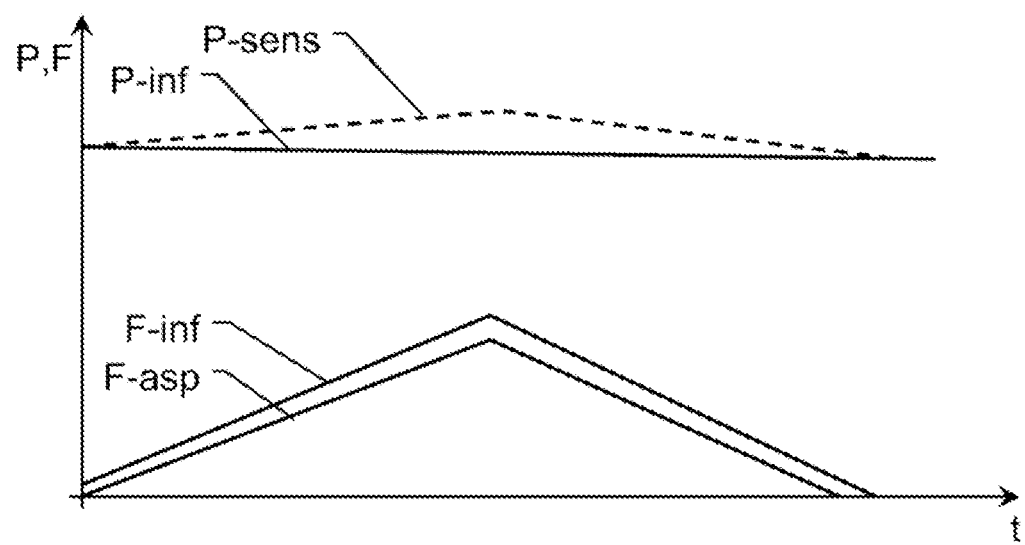

LIQUID MANAGEMENT IN AN OPHTHALMOLOGICAL DEVICE

This application is a 371 National Phase of PCT Application No. PCT/EP2017/078064, filed on Nov. 2, 2017; which claims priority to European Patent application 16197046.2 filed Nov. 3, 2016 and each of which is herein incorporated by reference in its entirety.

The invention relates to an ophthalmological device according to the preamble of claim 1 and an interchangeable part for an ophthalmological device according to the preamble of claim 10 as well as an associated method.

The invention relates to ophthalmic surgical equipment. In many cases, aspiration, i.e. the suction of eye liquid or particles removed during surgery, takes place during interventions inside the eye. For example, during cataract surgery, the clouded lens is removed from the eye and replaced by an intraocular lens (IOL). For example, a phacoemulsification (liquefaction of the lens nucleus) is performed in which surgical tools are inserted into the interior of the eye via an incision a few millimeters long in the area of the transition from the cornea to the dermis. A piece of the capsule is removed and then the lens contents are crushed and removed, e.g. with an ultrasound device or laser. The lens particles are removed by means of suction flushing connected to the surgical tool, which is a core element of the present invention.

This suction flushing aspirates the shattered lens nucleus particles and replaces the aspirated material with liquid infusion, for example with a Balanced Salt Solution (BSS). After removing the old lens core, a folded, elastic replacement lens is inserted into the capsular bag through the opening. The suction flushing is provided by an ophthalmological device, i.e. an operating device located in the operating theater which is operated by a doctor and/or nurse, usually together with other functions required for the operation. In addition to the phacoemulsification described above, the same medical devices with suction flushing function that are treated by this invention (or specific versions of such devices) are also used in other ophthalmological procedures in which an interocular infusion is often (but not necessarily) performed together with aspiration, for example in vitrectomy, diathermy, capsulotomy, glaucoma surgery, refractive surgery, femto-laser, etc. Documents DE 696 21 562, US 2016/045367, WO 02/056850 describe embodiment examples of such medical equipment.

US 2012/215160 proposes an infusion pressure measurement directly in the eye or on the handpiece. In addition to the pressure sensor unit directly at the eye required for this pressure measurement and the required data connection from the device to the eye, another disadvantage is that the dynamics of the system including the tubes between the device and the cassette are in the control loop and this must be designed accordingly. The need for a liquid reservoir with a movable wall for pressure control also complicates the system, increasing the liquid content and the system and sterile equipment parts.

In order to ensure sterility, intraocular infection or transmission from patient to patient must be safely avoided, especially with regard to aspirated liquid, which is potentially contaminated. This can be achieved, for example, by replacing an interchangeable insert, which is usually referred to as a cassette. These cassettes can be designed as disposable cassettes, daily cassettes and/or multiple sterilizable. In particular, the cassette contains those parts of the suction flushing that come or could come into contact with potentially contaminated patient liquid. These parts can be especially pump or suction devices, valves and/or sensors for pressure and vacuum, air bubbles, flow, etc. Connections-preferably mechanically coded to prevent interchanging—to lines to and/or from the patient, as well as for connections for waste and/or infusion containers, etc., are also usually part of such an interchangeable cassette, which is at least partially attached to or in the medical device in an interchangeable manner. The documents DE 693 09 757, DE 693 21 264, DE 696 15 507, DE 696 15 633, DE 697 09 192, U.S. Pat. Nos. 5,163,900, 5,282,787, 5,582,601, 5,800,396, 5,897,524, 5,899,674, WO 1987/001943, WO 2004/108189, or WO 2004/110524 show cassettes with similar properties.

Preferably, sensors, actuators, electronics and/or mechanics should be accommodated in the medical device and not in the interchangeable cassette. In particular, the cassette only forms the parts of the sensor system and the actuators that come into contact with potentially contaminated liquid, e.g. measuring chamber, membrane, pump or suction devices, squeezing areas of valves, etc.—especially passive parts. The active parts of sensors and actuators, especially if they represent a considerable cost factor, are preferably housed in the medical device.

For the suction flushing function, i.e. for infusion and/or aspiration—or in other words for the supply and removal of liquids in the eye—the surgical device or handpiece with which the eye is accessed has an aspiration line for aspiration and an infusion line to replace the aspirated and/or leaking liquid emerging through the insertion opening. In particular, the eye pressure (IOP=Inter Ocular Pressure) must be kept at least approximately constant during the operation. The eye, or an eye part such as the anterior chamber, should neither collapse nor be inflated during the procedure. Accordingly, parallel to the suction by aspiration, an infusion, i.e. supply of liquid, takes place at the same time.

In the prior art, the doctor usually prescribes a desired infusion pressure for the infusion. This is done with a fixed or motorized height-adjustable stand for the infusion bottle or bag. The difference in height between the patient and the bottle results in a hydrostatic pressure, which can be approximately 30 mbar above atmospheric pressure in the eye during such procedures.

Although such an infusion is easy to implement, it has certain disadvantages, for example the setting of a desired infusion pressure is rather static or can only be changed with very little dynamics. The reaction of the infusion pressure change is sluggish. For example, it is hardly possible or impossible on the part of the infusion to react to irregularities during an operation.

Systems are known in which compressed air can be blown into the infusion container to determine the infusion pressure. These, however, are complicated to handle, are more complex to connect, and carry the risk of loss of sterility. Changes in infusion pressure can also only be implemented slowly. For pressure reductions, special long cannulas are required, which protrude above the liquid level in the bottle. With this solution only special bottles can be used, which geometrically fit to the used cannula length.

It is an object of the present invention to improve an ophthalmological device or to provide an improved interchangeable cassette for such a device.

One object is to improve and simplify the infusion into the eye in particular, which, for example, takes place during a suction rinse during phacoemulsification.

In particular, it is an object to ensure a simple, safe and reliable maintenance of a desired eye pressure during an operation, especially in the case of unplanned occurrences.

The operability and manageability of the device should not be complicated but potentially simplified. It is also intended to reduce possible sources of error during handling as well as during the actual use of the ophthalmological device and/or cassette. A further object may also be to reduce or compensate for disadvantageous parasitic effects in prior art technology, such as pressure drop in the tubes, pressure reduction by air filters in the drip chamber, etc.

These objects are solved according to the invention by the features of the independent claims and/or by the features of the dependent claims or these solutions are developed further.

The present invention relates to an ophthalmological device which provides suction flushing having an aspiration function and an infusion function. It comprises an aspiration conveyor device for motor-driven discharge of liquid from a surgical instrument into a waste container. Thus, an active aspiration of liquid is provided from a patient to the waste container by means of a surgical intervention tool, which is not part of this invention. This conveyor device can in particular be in the form of a peristaltic pump or a vacuum suction unit.

According to the invention, the device also comprises an infusion conveyor device for the motor-driven feeding of an infusion medium from an infusion container to the surgical instrument. Thus, an active infusion is provided with a forced promotion of the infusion medium from the infusion medium storage container to a surgical intervention tool that is in contact with the patient. In this case, the infusion medium can be an infusion liquid, for example a BSS. The following description refers to infusion liquid as the infusion medium for ease of understanding, but this is not necessarily a restrictive view. Alternatively, a gas can be used as an infusion medium in a special embodiment. In addition to a gas container as an infusion container, especially when using air as an infusion medium, the OR can also function as an infusion container.

Specifically, the device comprises a control module adapted to provide an active infusion controlled by an infusion pressure and/or an infusion volume.

The infusion conveyor device can be specially designed as a peristaltic pump for active volume delivery of the infusion medium.

The areas of the infusion conveyor device and the aspiration conveyor device that come into contact with the liquid can be specially designed in a common interchangeable cassette for the device. The device may each have an associated infusion drive for the infusion conveyor device and, in particular separately, an associated aspiration drive for the aspiration conveyor device.

The design and dimensions of the aspiration conveyor device and the infusion conveyor device can be identical, in particular the same. In particular, this can be advantageous, as a similar control of the two conveyor devices also produces a similar volume conveyance.

Between the infusion conveyor device and the surgical instrument, a pressure measuring device may be provided with which an infusion pressure can be determined. The pressure measuring device can, for example, be designed with a flexible membrane in the interchangeable cassette and an associated pressure or force sensor in the device which, when the cassette is inserted, form an operative connection by means of which a pressure value of the infusion medium in the cassette can be determined. In particular, the determined infusion pressure can be adjusted to a target value by means of an automatic control of the infusion conveyor device—for example by means of a specially designed control unit in the device.

Between the infusion conveyor device and the surgical instrument, an optional ripple compensation may be provided, which is not absolutely necessary according to the invention. This can in particular be in the form of passive ripple compensation in the form of a flexible line area in the interchangeable cassette which, by means of elastic deformation of the flexible line area, compensates for fluctuations in the delivery volume and/or delivery pressure of the infusion conveyor device.

The ophthalmological device can also be equipped with a motor-driven height adjustment of the infusion container and a bypass valve device for optional bypassing of the infusion conveyor device. The bypass valve device in the interchangeable cassette can be passive, e.g. as a liquid channel squeezing area, and mechanically actuated by a valve drive in the device.

An air bubble sensor can also be installed along a path of the interchangeable cassette in which the infusion liquid is supplied. This can, for example, be equipped with a viewing window in the interchangeable cassette and an optical monitoring system in the device. This can prevent a falsification of a measured value of the infusion pressure, a reduction of the dynamics of an infusion pressure change by elastic air bubbles in the infusion system and/or an infusion of air into the eye. When filling the tube system, it is also possible to detect when the water column arrives at the cassette, which can, for example, shorten the filling cycle. This sensor can also be used to detect when only air comes out of the infusion bottle instead of BSS. An error message can then warn the OR staff and prompt them to connect a new BSS bottle before the eye collapses.

The infusion conveyor device can be formed with at least one squeezing channel, which is formed at least approximately in a circular arc and is made of an elastic material in the interchangeable cassette, the squeezing channel cross-section of which can be squeezed in a sealing manner by actuators on the device side by rolling at at least one point and this point is movable along the squeezing channel (94). In particular, a squeezing channel cross-sectional area along the uncrushed squeezing channel can be designed to vary. In particular, several squeezing channels can optionally be arranged hydraulically parallel and be controlled in a phase-shifted manner by a single infusion conveyor device in order to avoid ripple effects of the peristaltic pump.

An interchangeable cassette for an ophthalmological device in accordance with the invention can thus be designed with at least one rigid hard part as the housing of the interchangeable cassette and at least one elastic soft part. The hard part can in particular be made of a hard plastic, especially a thermoplastic such as polypropylene (PP) or polyethylene (PE). The soft part can in particular be made of an elastomer or a thermoplastic elastomer. At least one of the hard parts with at least one soft part can be designed as an integral multi-component injection-molded part. The hard part and the soft part form internal liquid channels of the interchangeable cassette, wherein the soft part is at least partially accessible from the outside. In particular, areas of the soft part are also formed as peristaltic pump squeezing channels on the cassette side for conveying infusion liquid in at least one of the liquid channels.

The soft part can form various functional elements of the interchangeable cassette. For example, at least one of the following:

a squeeze pump area for air or liquid in the liquid channels for volume delivery in the form of a peristaltic pump, a valve arrangement region for varying a flow cross-section in at least one of the liquid channels, a pressure sensor range for determining an air or liquid pressure in at least one of the liquid channels, and/or an optional ripple compensation range for compensating pressure and/or volume fluctuations of a liquid delivery by means of an elastic liquid channel range.

The interchangeable cassette can also at least be formed with:

a bottle connection for the connection of a container for the provision of infusion liquid, an infusion connection for supplying the infusion liquid to the ophthalmic surgical instrument an aspiration connection (50) for connecting at least one of said liquid channels to an ophthalmic surgical instrument, and a waste connection (55) for discharging liquid into a waste container (56), and/or an aspiration valve.

The invention also relates to a method for regulating the infusion pressure in an ophthalmological device, which can be carried out specifically as part of a suction flush. This involves active and specially motor-controlled aspiration volume delivery of an aspiration liquid from a patient to a waste container, and active and specially motor-controlled infusion volume delivery of an infusion liquid from an infusion container to the patient. The infusion volume delivery and the aspiration volume delivery can each be carried out by means of a peristaltic pump. Instead of the infusion liquid, the infusion conveyor device according to the invention can alternatively be used to deliver air instead of liquid for special applications in vitrectomy, i.e. a controlled infusion of air or another gas. This is described in more detail below.

This can involve measuring the infusion pressure of the infusion liquid (or alternatively, in special cases, of the infusion air) and regulating the delivery volume of the infusion volume delivery by means of the infusion pressure. In particular, this regulation can be carried out taking into account a pressure drop in a line to the eye, which is at least partially compensated by an increase in pressure during infusion volume delivery, so that the pressure desired in the eye actually prevails. According to the invention, this pressure drop can be determined by taking into account the flow rate of the infusion liquid in particular, since the flow rate can be determined on the basis of a current delivery volume of the infusion volume delivery. The pressure drop in the line, depending on the delivery volume, can be determined in a known way in a known line-especially as regards length and diameter—or the resulting flow velocity, e.g. by calculation, simulation or tests.

According to the invention, the delivery volume of the active infusion can also be adjusted to a characteristic value of the active aspiration. In particular, a dependency of a movement of an infusion peristaltic pump on a movement of an aspiration peristaltic pump can be implemented. In particular, an aspiration negative pressure can be determined during aspiration volume delivery and a temporary increase of the infusion pressure can be achieved if the aspiration negative pressure increases, for example in the case of aspiration occlusions. With this temporary increase of the infusion pressure, an undesired pressure reduction in the eye during the loosening of the aspiration occlusion can be counteracted.

For example, according to the invention, a method for controlling an active infusion in an ophthalmological device for suction flushing can be performed with a determination of an aspiration delivery rate of an aspiration of the suction flushing and a pilot control of an infusion delivery rate of the active infusion to balance the aspiration delivery rate. In addition, an infusion pressure of the active infusion can be determined and the pre-controlled infusion flow can be readjusted to achieve the desired infusion pressure.

Some of the methods described here are preferably provided at least in part as programmed sequences. The invention therefore also relates to computer program products with program code stored on a machine-readable carrier or provided as a computer data signal embodied by an electromagnetic wave (e.g. a radio signal) to perform the above method. The program code can carry out or be formed for automatic execution of the control and/or regulation tasks listed here, as well as operation sequences in an ophthalmological device.

The method and the device in accordance with the invention are described in detail below on the basis of concrete embodiment examples schematically depicted in the drawings, wherein further advantages of the invention are also discussed, wherein:

FIG. 1 shows a first block diagram of a first embodiment of an ophthalmological device according to the invention;

FIG. 2 a second block diagram of a second embodiment of an ophthalmological device according to the invention;

FIG. 3*a* and FIG. 3*b* show a first embodiment of an example of an interchangeable part according to the invention in the form of an interchangeable cassette for an ophthalmological device in 3D views from the left and right;

Figures 6A, 6B:
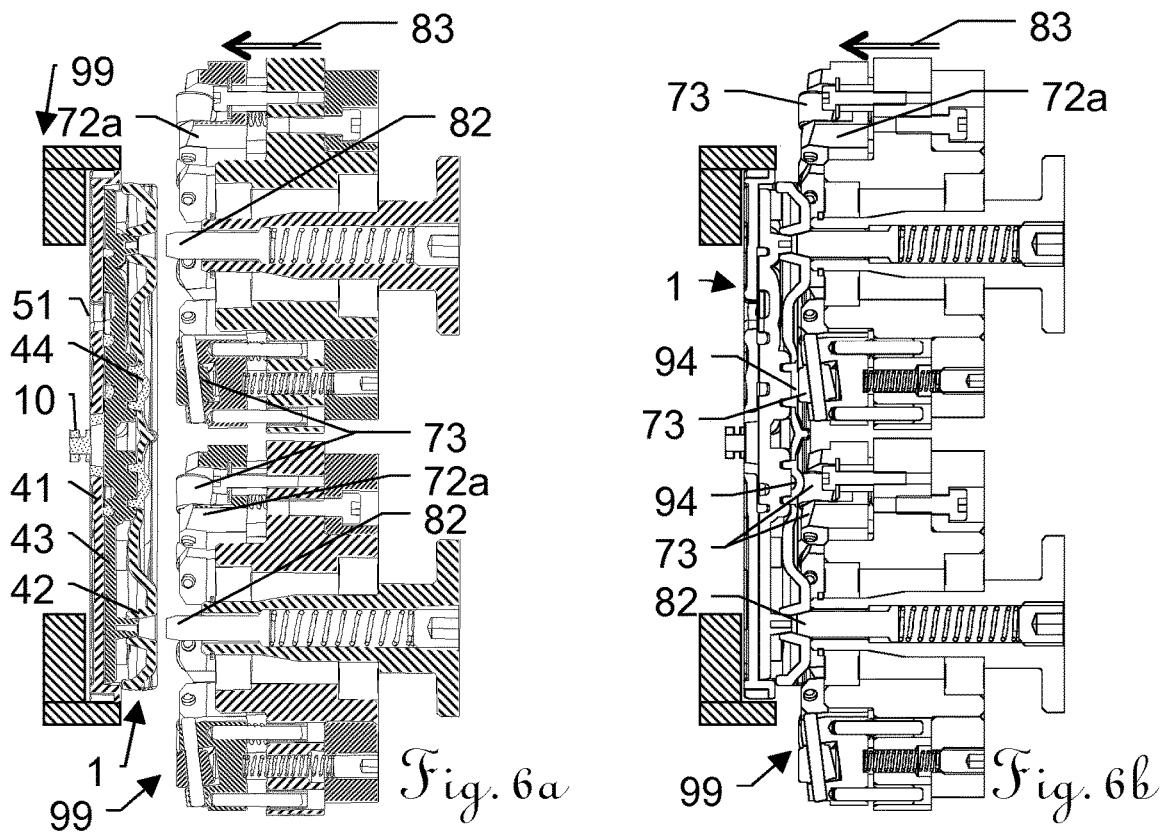
Figure 7A:
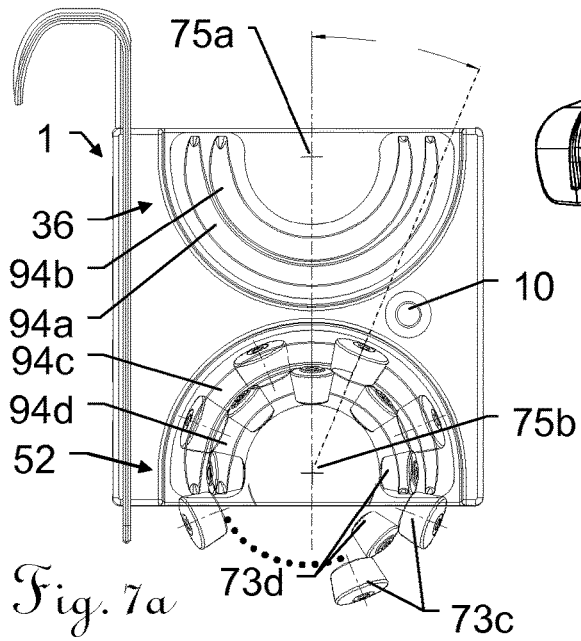
Figure 7B:
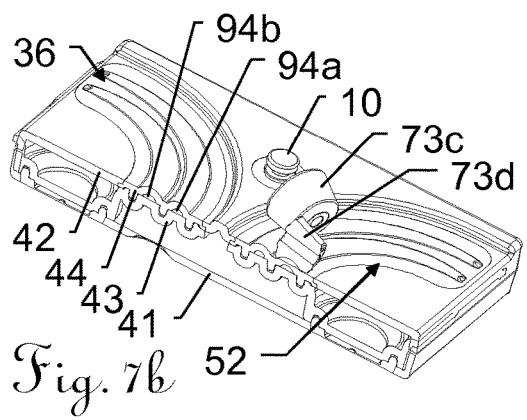
Figure 8A:
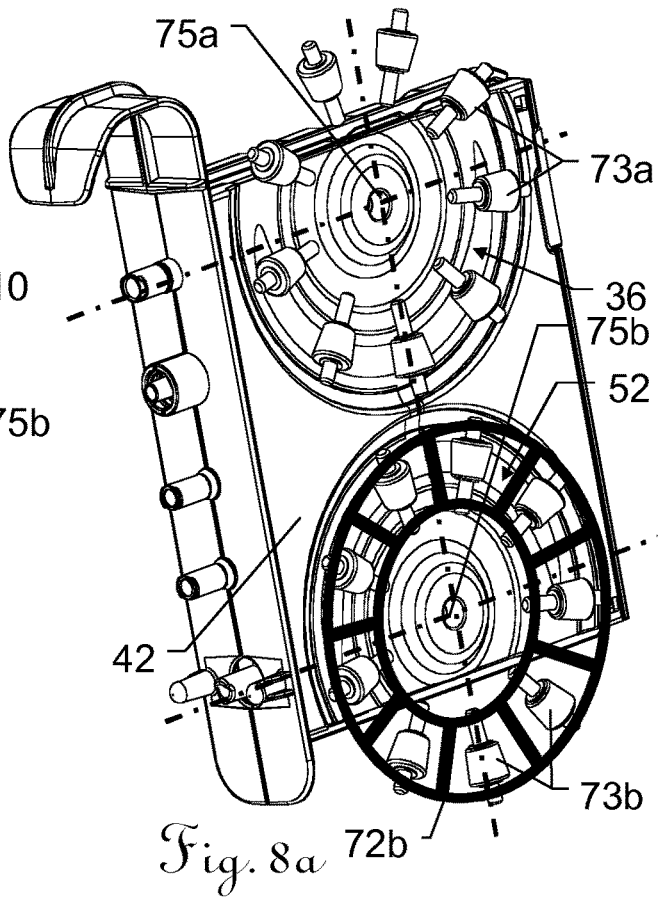
Figure 8B:
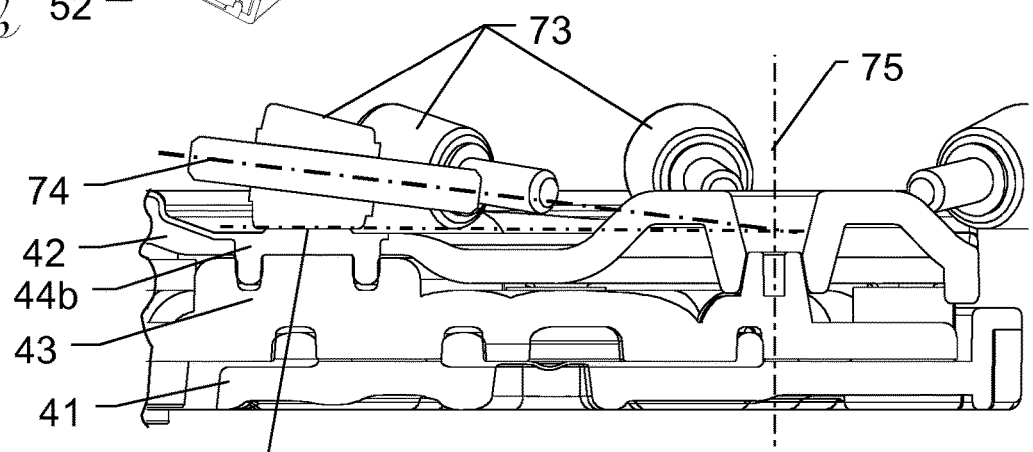

FIG. 6*a* and FIG. 6*b* show embodiments of examples of an interchangeable part according to the invention when inserted into the machine in a sectional view;

FIG. 7*a* and FIG. 7*b* show embodiments of an example of an interchangeable part according to the invention with an embodiment of an optional ripple reduction;

FIG. 8*a* and FIG. 8*b* show an illustration of an exemplary embodiment according to the invention of an interchangeable part with an active infusion conveyor device according to the invention;

FIG. 9 shows a first example of an embodiment of an active infusion in use according to the invention;

FIG. 10 shows a second example of an embodiment of an active infusion in use according to the invention.

The depictions in the figures are for illustration purposes only and, unless explicitly stated otherwise, are not to be regarded as true to scale. Identical or functionally similar features shall, as far as practicable, be consistently marked with the same reference numerals and, where appropriate, distinguished by a letter as an index. The diagrams show the basic technical structure, which can be supplemented or modified by a person skilled in the art according to general principles.

Figure 1:
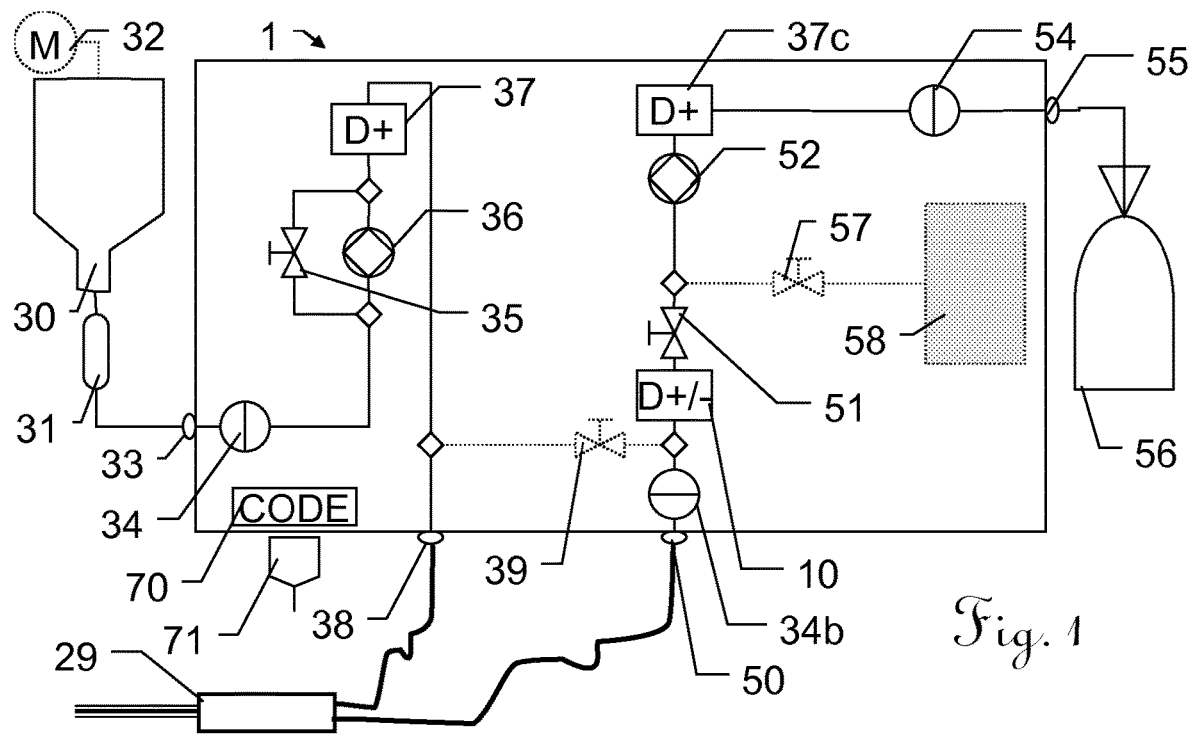

FIG. 1 shows a possible example of a block diagram of an embodiment of an ophthalmological cassette 1 according to the invention with at least one active infusion according to the invention. In this example, it can be specifically an infusion device in an interchangeable cassette 1 of an ophthalmological device 99, with which suction flushing can be carried out. In the left half of the figure an active infusion device is shown, in the right half an aspiration device.

A container 30, e.g. an infusion bottle or an infusion bag, provides an infusion liquid, e.g. a BSS (Balanced Salt Solution) or another infusion liquid. This infusion liquid supply can, for example, be equipped with a device for checking the filling level. For example, the container 30, a drip chamber 31, a connection tube and or a cassette-internal liquid channel with a wired or wireless sensor can be monitored for emptying. When cassette 1 is inserted, connection 33 can be arranged on cassette 1 so that it can be accessed from the outside and connected to the infusion container 30 or the interposed drip chamber via a tube, for example.

As known from the prior art, the infusion liquid pressure at the bottle connection 33 of cassette 1 (or in the entire infusion system) can optionally be changed by varying the height of the container suspension by means of a height adjustment of the suspension of container 30, preferably motorized and automatic, which is symbolized here by the drive 32. However, with the active infusion according to the invention, this height adjustment is not absolutely necessary but can be provided as a switchable option and/or as additional safety or redundancy on the device according to the invention.

In the case of another embodiment of a cassette 1 according to the invention, an active infusion can, according to the invention, be carried out exclusively by means of an active liquid conveyor device 36. A pumping device, such as a peristaltic pump or another liquid delivery device in the infusion system, is designed for this purpose. With such an embodiment, an infusion valve 35 and/or a height adjustment of the infusion container 30 can optionally be dispensed with. The infusion pressure and/or the delivery volume of the infusion can be varied, in particular controlled or regulated, by appropriate control of the conveyor device 36.

Another preferred embodiment of a cassette 1 according to the invention can also have—as shown in the figure-both an infusion container height adjustment 32 and an infusion liquid conveyor device 36. Cassette 1 according to the invention can be designed in such a way that the infusion pressure can additionally be adjusted or regulated as described here by changing the height difference between the container 30 of the infusion site. In particular, a valve 35 can be designed as a bypass to the conveyor device 36. Thus, with the same cassette 1, either an active infusion pressure variation (i.e. actively initiated by the conveyor device 36) or a hydrostatic infusion pressure variation (i.e. caused by a difference in height) can be provided. In particular, if required, it is possible to switch seamlessly between these two principles—e.g. also during operation—for example according to the current requirements of the operation being performed or according to the surgeon's preferences. Special applications in which two different and independent infusion pressures are required at the same time can also be carried out with such an embodiment according to the invention by applying a first pressure-adjustable infusion by means of the hydrostatic height adjustment via a first line to the eye and a second pressure-adjustable infusion with the active infusion by means of the infusion conveyor device in the cassette via a second line to the eye.

The infusion system according to the invention can also have an infusion pressure measuring device 37, by means of which a pressure in the infusion system can be determined, monitored and/or regulated. Preferably, this infusion pressure measuring device 37 is arranged after the infusion valve 35 and/or the pumping device 36, so that their determined pressure corresponds to that which is supplied to the eye. Since the infusion system can (or at least should) only have overpressure in relation to the atmosphere, this infusion pressure measuring device can be designed in such a way that only overpressure can be determined with it, and not necessarily underpressure (although such a variant would also be applicable). One of many possible examples of a concrete embodiment can be formed, for example, with a part of the infusion liquid channel that has been extended to form a pressure chamber and has a flexible membrane on the outside. When cassette 1 is inserted, this membrane is in contact with a sensitivity surface of a force or pressure sensor in the device 99. The force exerted on the membrane by an overpressure in the liquid channel relative to the atmosphere can thus be determined as a measured value for the overpressure in the liquid channel.

The infusion liquid is provided by means of the cassette 1 according to the invention with active infusion according to the invention with adjustable pressure and/or delivery volume at an external infusion connection 38 of the cassette 1, which can be connected to a line or a tube to the surgical intervention tool, e.g. the surgical handpiece 29, so that the infusion into the eye can be provided with adjustable and/or regulatable pressure and/or volume. In order to guarantee safety, the actual prevailing pressure of the infusion to the patient can be monitored with a corresponding pressure sensor 37. If necessary, pressure losses in the line system to the patient can also be taken into account-especially pressure losses due to dynamics, since the delivery volume and thus also the flow rate of the infusion are known according to the invention by the conveyor device 36.

In particular, the infusion liquid, for example, can be provided by means of the cassette 1 according to the invention with active infusion according to the invention with adjustable delivery volume via a volume conveyor device with a defined, known delivery volume at an external infusion connection 38 of the cassette 1, which connection can be connected with a line or a tube to the surgical intervention tool. In order to provide the infusion into the eye with adjustable pressure, the actual prevailing pressure of the infusion towards the patient is monitored with a corresponding pressure sensor 37 in the device. According to the invention, pressure losses in the line system to the patient can also be taken into account, especially pressure losses due to dynamics, since, according to the invention, the delivery volume and thus also the flow rate of the infusion in the line is known through the conveyor device, on which flow rate a difference between the pressure value at different ends of the line depends in a known way. Especially if a tube diameter, a tube cross-section and/or a tube length of the line are known—which is usually the case with such interchangeable cassettes or sets—a resulting pressure on the eye can be well regulated under consideration of the delivery volume. In particular, with such a direct control of the delivery volume, taking into account the pressure losses in the line, a direct and thus very fast pressure control can be achieved, which has advantageous dynamic characteristic values for this application.

According to a partial aspect of the invention, the arrangement and formation of the liquid channels within cassette 1 is preferably such that when the liquid channels are filled with liquid, this filling always takes place (at least substantially) from bottom to top—with which any air bubbles (corresponding to the medium density ratio) are displaced upwards and discharged away from the patient and an accumulation of air bubbles is avoided. Such a filling of the liquid channels of cassette 1 takes place especially after the insertion of cassette 1 when it is put into operation. For example, according to this aspect of the invention, the arrangement of the connections can be designed from bottom to top in the following order: waste bag 55—aspiration-A from patient 12a, 50—optional aspiration-B 12b—infusion to patient 38—infusion bottle 33.

The cassette 1 according to the invention can have at least one air bubble sensor 34 in the infusion system, with which a correct function can be monitored and an infusion of air can be avoided. The air bubble detector 34 can work in particular optically—for example due to different light refraction properties of air and liquid, or also on other principles, with which a distinction can be made between the presence of gas or liquid in the infusion system. For example, the principle of different angles of total reflection of liquid compared to air, different light conduction properties of liquid and air, or another active principle, such as a capacitive one, can be used. One example of a concrete embodiment can be formed with a viewing window into the liquid channel that is optically transparent at least in the wavelength used, which can be implemented in an outer shell 41, 42 of cassette 1. In one embodiment, for example, the outer shell can be made of transparent material.

Also shown here is an optional path according to the invention from the infusion system to the aspiration system of cassette 1, which can be released with a venting valve 39. This can be used, for example, to fill the aspiration system with liquid, especially when cassette 1 is put into operation, and/or to backflush infusion liquid through the aspiration system, for example to loosen occlusions (reflux) or generally to reduce the negative pressure in the aspiration path, e.g. if the physician wishes to reduce the desired negative pressure via the foot switch. For these functionalities, further valves may be available in the cassette for the corresponding switching of the liquid flows.

The aspiration system of the cassette 1 according to the invention is connected to the surgical intervention tool 29 via an aspiration connection 50 with a pipe or tube. Again, at least one air bubble sensor 34b can be present in the aspiration system. The figure also shows an aspiration valve 51. In the aspiration system, a pressure measurement can also be carried out with a pressure measuring device 10, which can, however, measure both negative and positive pressures with respect to the atmosphere. In order to detect forces in both positive and negative directions accordingly, the pressure measuring membrane of the cassette must be connected to the corresponding pressure measuring sensor in the device to transmit both positive and negative values. Examples of such known pressure detection devices can be found, for example, in patent application EP 16197018 filed on the same day by the same applicant, which is hereby included by reference, or possibly also in the references cited therein.

To achieve the aspiration effect, the figure shows two variants, i.e. on the one hand a peristaltic aspiration and on the other hand a Venturi aspiration. An embodiment of a cassette 1 according to the invention may either exhibit only peristaltic aspiration, or another embodiment of cassette 1 according to the invention may comprise only Venturi aspiration, or another embodiment according to the invention may comprise both peristaltic aspiration and Venturi aspiration.

In Venturi aspiration, the aspiration effect is caused by an air vacuum, which is usually generated by a name-giving Venturi nozzle or a vacuum pump. These variants are symbolized here by the Venturi valve 57 and the vacuum system 58. In particular, a so-called "Clean Venturi" system can also be applied, which is described in the international application EP 16196998 filed on the same day by the same applicant and is hereby included by reference. In the case of Venturi aspiration, a measured value of the aspiration vacuum in particular can be used as the basis for controlling the active infusion conveyor device 36, e.g. as described below. In particular, the active infusion conveyor device 36 according to the invention can be controlled and/or regulated on the basis of currently prevailing infusion pressure and currently prevailing aspiration vacuum by a control unit provided for this purpose. Optionally or alternatively, the control unit can also include values of a current delivery rate of the infusion and/or aspiration.

In peristaltic aspiration, a liquid conveyor device 52 is used to generate the aspiration effect. The delivery device 52 can in particular be a peristaltic pump, but optionally a membrane pump or other liquid delivery devices can also be used. The aspirated liquid is preferably pumped into an appropriate waste container 56, which is preferably connected to an appropriate waste connection 55 outside cassette 1. Again, a pressure sensor 37c, especially for overpressure, can be used to detect a pressure increase with a full waste bag.

Cassette 1, in accordance with the invention, may also have a coding 70, in particular mechanical and/or optical, which can be recorded and evaluated by a corresponding reading unit 71 of the device 99. This coding can be used to prevent multiple or non-sterile use, for example with disposable cassettes, and a specific embodiment of the inserted cassette and its optional functionalities etc. can be detected by the device 99.

In special vitrectomy procedures, when the vitreous body is removed, a gas, usually room air cleaned with a bacteria filter from the OR, is first pumped into the eye, usually with an overpressure of approximately 20 to 120 mmHg. As a result, this pumped-in air is then replaced by a silicone oil, which presses the detached retina back onto the choroid so that it can grow back again. In the prior art, an air pump specially designed for this purpose is required in the device for this purpose, which, however, is very rarely actually used. If a peristaltic pump is used specifically for infusion as the active conveyor device 36 in accordance with the invention, this pump can also be used for conveying gases instead of infusion liquid. This not only results in a simpler device design by dispensing with the special air pumping device but also has advantages in terms of hygiene and sterility, as the interchangeable cassette 1 is sterilized and is also regularly replaced. As an optional accessory, a preferably sterile and/or single-use bacteria filter can, for example, be attached to the bottle connection of interchangeable cassette 1, which filters the infusion air sucked in in this case.

Figure 2:
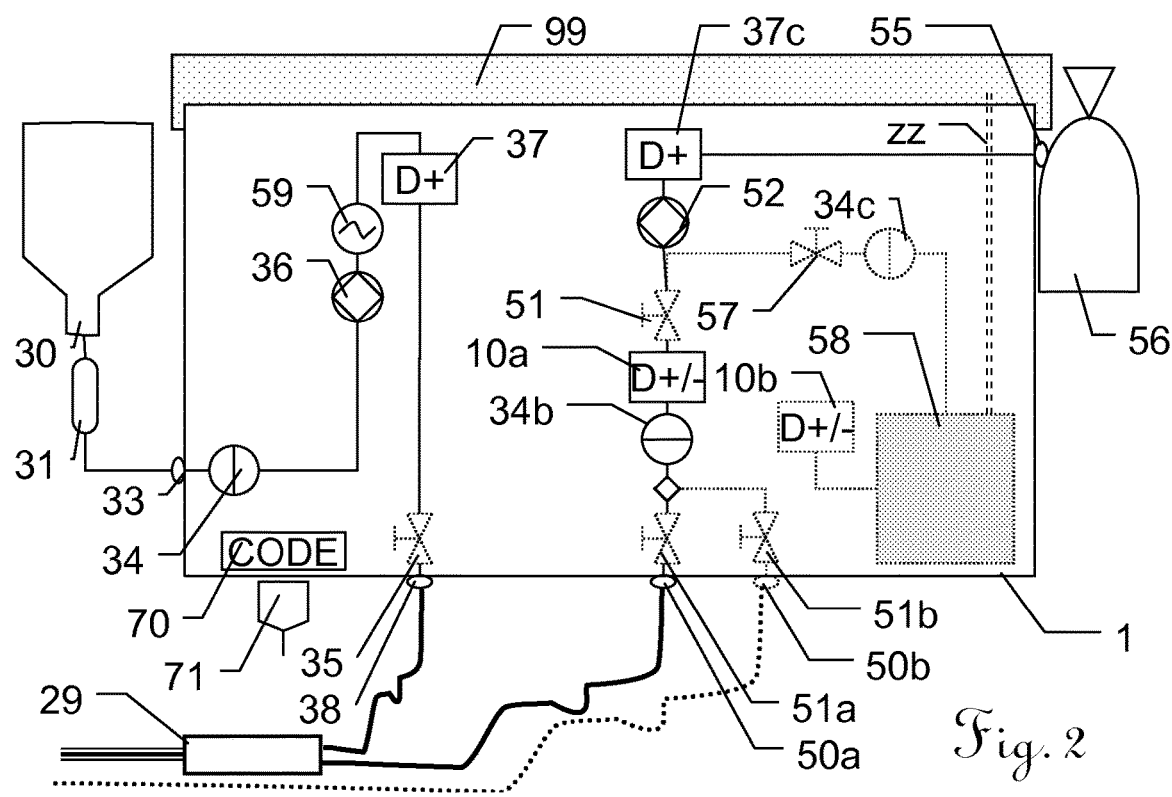

FIG. 2 shows another exemplary embodiment of a cassette 1 according to the invention in a block diagram. The features functionally identical or equivalent to FIG. 1 are provided with the same reference numerals and reference is made to their description above.

The main differences between this embodiment according to the invention and FIG. 1 are, according to the invention, that in the infusion area only one active infusion is carried out by means of a conveyor device 36. The infusion valve 35 is here only optionally designed as an additional shut-off against the patient—but can also be omitted, especially if the liquid conveyor device 36 already has a sealing effect. The infusion path additionally shows an optional passive or active ripple compensation element 59 for a peristaltic pump 36, which is not absolutely necessary according to the invention. A passive compensation can, for example, be formed with a flexible area of the liquid channel which has the effect of a balancing bellows which cushions the pressure or flow rate ripple by deforming according to the ripple. Alternatively or additionally, active ripple compensation can be applied, in which an actuator on the device side deforms a flexible area of an infusion liquid channel and thereby compensates for pressure or flow rate ripple effects. The actuator can be controlled, for example, on the basis of values from the pressure sensor 37 and/or information about the rotary position of the peristaltic pump 36. According to the invention, a dynamic variation of the rotational speed of the peristaltic pump can also take place in such a way that the ripple effect of the conveyor device is minimized. In contrast to a normal, uniform rotational movement (with an optionally accelerated or decelerated phase in the case of changes in flow rate) as applied in the prior art, no strictly uniform rotational movement of the roller head takes place during conveying, but the rotational speed is modulated with the period duration of the roller interventions in such a way that the flow rate ripples occurring with this period duration are compensated as far as possible. Thus, a temporary acceleration or deceleration of the roller head movement occurs when a roller enters the area of the inlet or outlet of the squeezing channel (inlet or outlet, depending on which side of the ripple is to be compensated, i.e. when feeding or suctioning).

In the aspiration area, the waste bag 56 can be attached directly to cassette 1 in accordance with the invention. In addition to the aspiration connection 50a, a second, optional aspiration connection 50b with corresponding aspiration valves 51b and 50b is also shown for selection. In a Venturi system, the optional pressure sensor 10b can additionally monitor the pressure in the suction chamber of said system.

According to the invention, the infusion pressure can also be adjusted much more quickly than is possible with prior art technology. This can be done in particular depending on the surgical step or special circumstances that occur during the operation.

With the data known according to the invention which relate to the flow rate of the active infusion as well as the aspiration, the tightness of the incisions (=opening in the eye) can also be determined and this information can be made available for display or further processing.

The embodiments of an active infusion according to the invention described here offer a number of advantages over a known infusion system, such as a gravity infusion or an infusion by pumping air into the infusion surface. In particular, an active infusion according to the invention, especially with a peristaltic pump, offers advantages such as:

Simplification of the setup of the operation and the commissioning of the device—and thus time saving, especially since an initial filling of the infusion system is designed significantly easier and faster.

Reduced risk of sterility errors, especially when setting up the device.

Faster pressure changes during the intervention than in the prior art can be carried out, which offers many application possibilities not known until then.

Independence from a special supply of the infusion liquid, especially with regard to bottle size and bottle type, as this has no effect on the active infusion according to the invention.

Additional monitoring functionalities, parameter evaluations, safety and comfort functions, etc. can be implemented.

There is less waste because air filters, long needles for the infusion set, tubes, packaging etc. can be saved. Only the interchangeable cassette, which is required for aspiration anyway, is required, which can optionally be designed to be sterilizable several times. The costs of consumables will also be reduced.

Figure 3A:
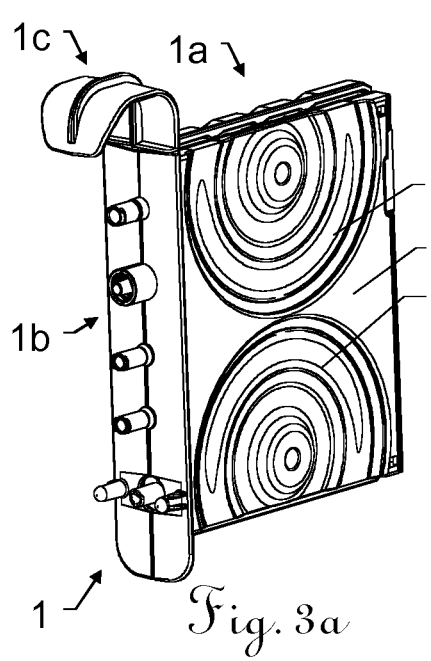
Figure 3B:
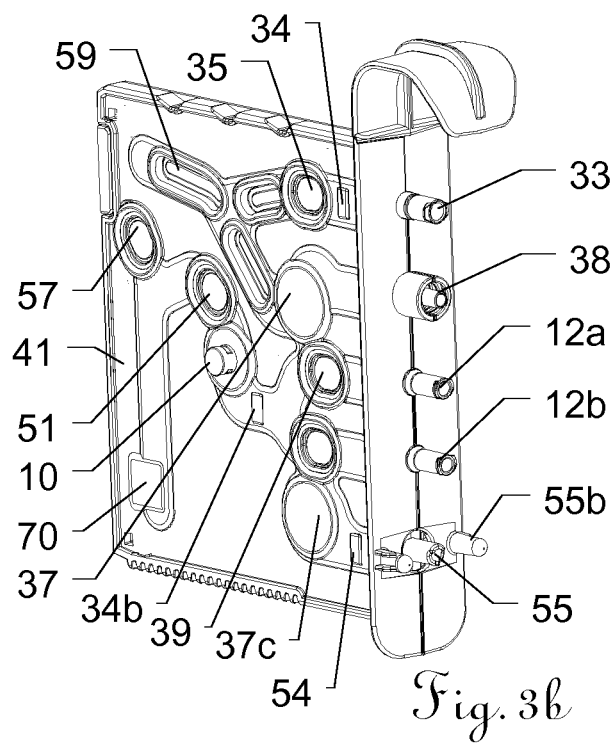

FIG. 3a and FIG. 3b show a further embodiment of a cassette 1 according to the invention, each in a view from the right and left front. In the figures, the functional elements already described in the block diagram are shown and marked again. In this example, cassette 1 is shown as a basic cassette 1a, at least approximately cuboid in shape in its outer contours, with a projecting plate as the front section 1b. On the front section 1b there are connections for tube systems, in particular those to the surgical handpiece, to the infusion liquid reservoir 30, and to a waste bag 56. Preferably these connections 33, 38, 50, 55 are mechanically and/or geometrically coded as shown in order to exclude the danger of incorrect connection and confusion.

In the example of an embodiment shown here, the functional elements of cassette 1 are divided between both of the shown outer shell halves 41 and 42 of cassette 1, thus enabling a compact structure to be achieved. The squeeze pump sections 36 and 52 are especially arranged on one cassette side 42, and the valves and pressure sensors are arranged on the opposite cassette side 41. Such a division of the functional elements is not mandatory, but can be advantageous with regard to gripping or clamping cassette 1 in device 99, in which clamping, fixing and/or fine positioning of cassette 1 in device 99 can take place simultaneously with pressing of the roller head(s) of the peristaltic pump. The movement required to clamp the cassette in the device 99 can only be carried out from one side, preferably from the side of the peristaltic rolls. The following figures illustrate in detail another exemplary design of a peristaltic pump according to the invention of a cassette 1 according to the invention.

Figure 4:
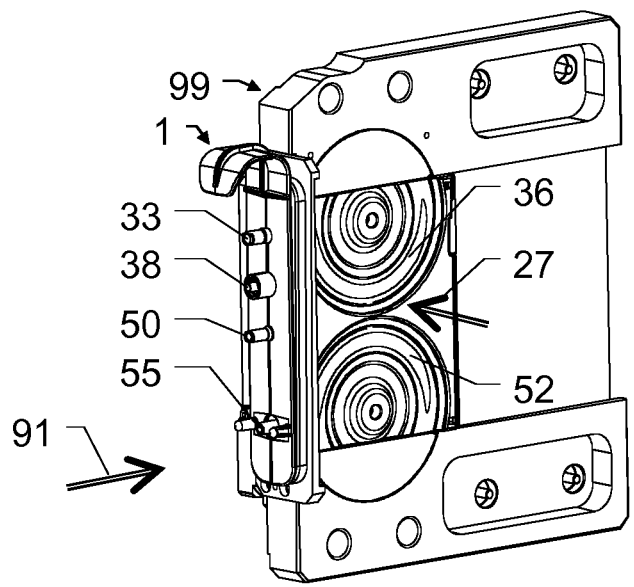
FIG. 4 shows a representation of an exemplary embodiment of an interchangeable part according to the invention, which is inserted in an appropriate example of an ophthalmological device in accordance with the invention.

FIG. 4 shows an exemplary embodiment of a cassette 1 according to the invention in its end position in a cassette slot of a device 99. Cassette 1 was inserted by pushing it into the cassette slot in insertion direction 91 and can be done manually or at least partially automated or motorized. A part of the cassette slot is shown as a section, but cassette 1 is shown in a non-sectional manner. In the illustrated position of cassette 1 in device 99, rollers can press against the squeezing areas of peristaltic pumps 36 and/or 52, essentially orthogonal to the shown side of cassette 1 in direction 27, so that cassette 1 can be positioned and fixed according to the invention in device 99 at the same time. In this inserted state, the sensors and actuators on the device side are in a position with respect to the cassette in which they can interact with their respective associated functional elements of cassette 1 for the intended purpose.

Figure 5:
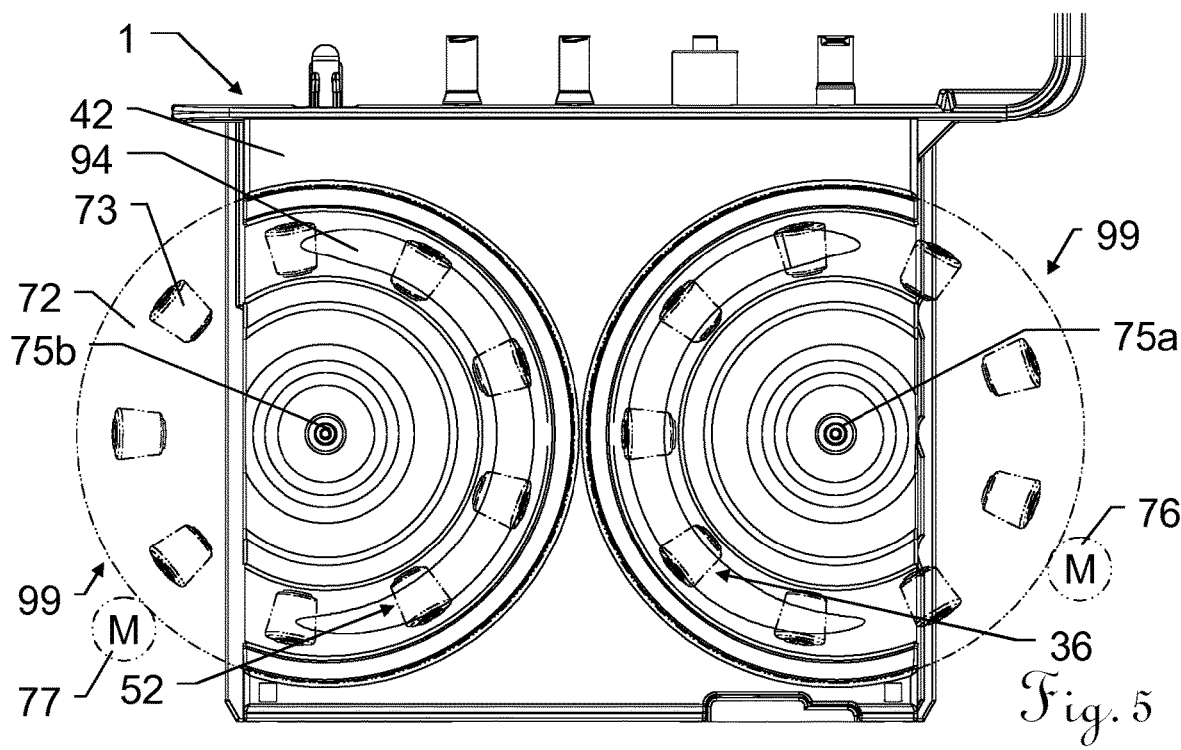
FIG. 5 shows a superimposed view of an embodiment of an infusion liquid delivery according to the invention.

FIG. 5 schematically shows such a clamping and fixing of the inserted cassette 1 in the device 99 in a side elevation view, with viewing direction at the peristaltic pumps of cassette 1 (direction 27 in FIG. 4). A roller head 72 on the device side with rollers 73 is shown, which rollers 73 roll on the bulging squeezing area 94 of the outer shell 42, which is formed of elastic soft plastic 44. With this unrolling, the squeezing area 94 is pressed by the rollers 73 sealingly onto the core part 43 of cassette 1 and, with a rotation of the roller head 72 around the rotation center 75, a volume in the squeezing area 94 between the rollers 73 is conveyed. For the rotation of the roller heads 72, the device 99 has a respective infusion drive 76 for the infusion conveyor device 36 and an aspiration drive 77 for the aspiration conveyor device 52.

In FIG. 6a, cassette 1 is inserted in insertion direction 91, which in this figure runs orthogonally to the drawing plane, into device 99 up to its end position, but is not yet clamped. This concerns a sectional view of the right and left rotation centers 75a and 75b of the two separate peristaltic pumps 36 and 52 from FIG. 5. In the example shown, cassette 1 shown in the section is essentially made up of three parts, with a left outer shell 41, a right outer shell 42 and a core part 43. Preferably the outer shells 41 and 42 are designed to be snapable, compressible or squeezable against each other and/or against the core part 43, e.g. with a hook system, a press-fit system or similar, which in particular cannot be designed to be detachable again. In this case, the outer shells 41 and 42 can in particular be designed as two-component injection-molded parts consisting of a rigid hard plastic component and an elastic soft plastic component. The elastic soft plastic part is then clamped and squeezed and/or positively engaged with the core part 43 so that the liquid channels or pipes are formed and sealed within cassette 1. In the section shown, the elastic portion 44 forms beads along the liquid channels which, in the assembled state, engage in depression in the core part 43—thereby effecting a liquid seal, in particular by squeezing the soft plastic 44 and/or forming a meander seal with at least one step. Partial areas of the soft plastic part 44 are accessible from the outside when cassette 1 is assembled and form the functional elements. The hard plastic part of the two-component injection-molded outer shells 41 and 42 has corresponding cut-outs for this which provide access to the soft plastic 44. Optional sterilizability of the entire cassette, for example in the autocalve, etc., can also be taken into account when selecting the cassette materials if a reusable embodiment is desired.

In this example of an embodiment according to the invention, cassette 1 is clamped after insertion and the roller heads 72 of the peristaltic pump are pressed in direction 83. As shown, the clamping force of the rollers 73 and/or the position alignment 82 can be determined by means of springs.

The actuators which are not visible here and which act on the valves 35, 39, 51, 51a, 51b and/or 57 are also arranged in device 99 in accordance with the invention and are designed, for example, as electromagnetically or electromotively or pneumatically actuated plungers in the device which act mechanically on the valve formations of cassette 1. The pressure sensing device 10, especially its coupling element, is also coupled in the inserted state of cassette 1 with the force sensor 11 on the device side, which is not shown here. As also the membrane on the cassette side of the pressure sensor 37 and/or 37c is brought into a functional operative connection with a force or pressure sensor on the device side.

FIG. 6b shows cassette 1 in clamped state in device 99, in which all sensors and actuators of device 99 correspond with their counterparts of cassette 1 for interaction. In the example shown, this is done by clamping cassette 1 in device 99 by pressing roller heads 72 against cassette in direction 83. Thus the cassette 1 is pressed in the drawing level to the left on corresponding mechanical stops. The rollers 73 squeeze the squeezing channels 94—wherein in the upper pump (e.g. the infusion pump 36) there is a section through the roller 73 with a squeezed squeeze cross-section 94 and in the lower pump (e.g. the aspiration pump 52) there is a section next to a roller 73 and correspondingly an unsqueezed squeezing cross-section 94. With the centering elements 82, which in this example also form the rotation axis 75 of the roller head 72, fine positioning of cassette 1 in device 99 is also achieved when cassette 1 is clamped.

FIG. 7a shows an exemplary embodiment of a cassette 1 according to the invention in which a cassette-side pumping device 36 for the active infusion according to the invention and a further pumping device 52 are shown.

The illustration shows a first pumping device 36 for infusion and a second pumping device 52 for aspiration, separate from the first pumping device. These pumping devices are formed with the soft areas 44 of the outer shell 42, which form outwardly curved squeezing channels 94. As a result of the intervention of rollers 73, these squeezing channels 94 are pressed locally sealingly onto the core part 43. By moving the roller 73 along the squeezing channels 94 a volume can be conveyed in the squeezing channels 94. This movement can be achieved by rotating a roller head 72 around the rotation axis 75b, wherein the roller head 72 carries the rollers 73a and 73b. Especially shown are the rollers 73c and 73d on the device side, which move on concentric circular paths and engage in the respectively assigned squeezing channels 94c and 94d on the cassette side and form the pumping device 52 in cooperation with these. The same applies to the pumping device 36, wherein for the sake of clarity the rollers assigned to the squeezing channels 94a and 94b are not shown here.

A partial aspect that can be carried out according to the invention in this specially further developed embodiment for the reduction of ripple effects is the dual pump design with at least two adjacent squeezing areas 94c and 94d. These are designed and arranged in such a way that the ripple of the two adjacent squeezing channels 94c and 94d occurring due to the squeezing pumping effect is compensated as much as possible and thus the overall ripple of the pump is reduced. As shown, this can be achieved, for example, by mutually offset squeezing rollers 73c and 73d, which cause a phase shift of the pressure or flow rate ripple generated by the two squeezing channels 94c and 94d. The two inlets and the two outlets of the squeezing channels 94c and 94d are hydraulically connected to each other. In particular, a phase shift of the ripple curves by approx. 180 degrees for two channels can result in an advantageous reduction. With a different number of squeezing channels 94, the phase shift must be selected accordingly in a different manner. Alternatively or additionally, the position and/or shape of the inlets and/or outlets of the two squeezing areas 94 can be designed differently in order to effect said phase offset and/or a further ripple reduction. Thus, a ripple reduction can be achieved in relation to a single squeezing area according to such a further developed embodiment with a corresponding design.

In the case of an at least near concentric arrangement of two interconnected squeezing channels 94c and 94d which are shown here, it can also be considered that with their different arc radii also different arc lengths occur. For ripple compensation, the liquid channel cross-sectional dimensions, cross-sectional shapes and/or cross-sectional progressions of the outer arc 94c can therefore be designed in accordance with the invention so differently from the inner arc 94d that the volume conveyed per movement unit of the rollers 73 always remains at least approximately the same— or the volumes always balance each other out as far as possible and together result in the smallest possible ripple of the total volume conveyed, e.g. in such a way that over a complete revolution of the roller head carrying the rollers 73, the outer and the inner squeezing paths 94c and 94d convey at least approximately the same volume or have as far as possible a diametrically opposed volume ripple. Due to optionally different diameters of the engaging rollers 73c and 73d, different squeezing radii can also be taken into account in these considerations.

FIG. 7b shows the embodiment of FIG. 7a again in a sectional view through cassette 1. The liquid channels in the area of the peristaltic pump are formed in the interior of cassette 1 by the hard plastic core part 43, over which an elastomer part 44a of the outer shell 42 curved towards the exterior of cassette 1 forms a partial area of the liquid channel. This partial area, which is also referred to as squeezing area 94 of the pump, can be squeezed by engaging rollers 73 on the device side in the mode of action of a peristaltic pump so that the liquid or air in the liquid channel can be pumped when the roller 73 is moving. In particular, according to the invention, the cross-sectional area of the squeezing area 94 formed in this case can vary over its length. As shown in this example of an embodiment according to the invention, a taper of the cross-section towards the outlet of the pump and/or an enlargement or reduction of the (unsqueezed) cross-section at the inlet of the pump may be possible. In particular, an optimization of this change in cross-section can minimize pressure and/or flow rate fluctuations (also known as ripple) during conveying. An advantageous cross-sectional profile along the squeezing area 94 can also be determined, for example, by means of simulation and/or test series.

FIG. 8a shows cassette 1 with exemplary roller heads 72 in engagement. For the sake of clarity, only the lower rotatable roller head 72b, to which the rollers 73b are attached, is indicated in the figure—in the case of the upper pumping device, only the rollers 73a but not the associated roller head 72a are shown. In the example shown here, a first roller head 72a and a second roller head 72b of the respective separate infusion and aspiration pumps intervene on the same side of cassette 1. In another embodiment, the first and second roller heads 72a and 72b can also engage on opposite sides of cassette 1. In particular, but not necessarily, the rotary axes of the roller heads can be arranged opposite each other and form an at least approximately common rotary axis, which can bring advantages with regard to force distribution on cassette 1.

In this embodiment according to the invention, the squeezing areas are each only single, i.e. formed without a hydraulically parallel second squeezing channel as in the previous embodiment from FIGS. 7a and 7b.

In the example of the embodiment according to the invention shown here the two pumps 36 and 52 describe in each case at least approximately a semicircle on cassette 1. This results in an advantageous use of space on cassette 1 shown here by way of example, especially with simple handling and producibility. A concentric arrangement of the two pumps 36 and 52, which can also be implemented, would also be possible but would be comparatively more complex in terms of design. Alternatively, the beaded squeezing area 94 of the pump 36 and/or 52 can also be designed in a different embodiment with a different, in particular shorter arc length, wherein, however, an appropriate arrangement and number of rollers 73a or 73b must always be selected so that sufficient pumping behavior can be ensured, i.e. in particular in each squeezing area 94, at least one, preferably more than one, roller 73a is always engaged.

As illustrated in FIG. 8b, this can be achieved, for example, in accordance with the invention, by arranging the roller axes 74 at an angle to their unrolling planes on the squeezing channels 94, and preferably intersecting with this unrolling plane in the center of rotation 75 of the roller head 72 carrying the rollers 73. The frustoconical rollers 73 thus roll optimally onto the soft plastic area 44b of the outer shell 42, which forms the squeezing channels 94, and squeeze this against the core part 43. Alternatively, other geometries can also be used. The forming and arrangement are preferably carried out in such a way that the circumference of the roller 73a or 73b at one point is respectively proportional to the circumference of the circular path described by the roller at this point around the pivot 75a of the center of the roller head 72a.

FIG. 9 shows an exemplary embodiment of an example of an interdependent control according to the invention of the infusion conveyor device and aspiration conveyor device according to the invention. At the beginning the "normal state" is shown, where the infusion pressure P-inf is at least approximately constant and the aspiration volume V-asp is also at least approximately constant—e.g. an aspiration peristaltic pump rotates at an average constant speed. As a bar on the abscissa, which represents a time axis, an occlusion of the aspiration tool is shown, i.e. when a shattered lens particle clogs the tip of the suction needle, for example. This causes the aspiration negative pressure in the device to rise as shown on the corresponding curve. In accordance with the special partial aspect according to the invention described here, the infusion pressure can now be increased as a precaution in such a case with the rapid, dynamic controllability of the infusion pressure with the infusion conveyor device according to the invention from a certain aspiration vacuum, as shown in the corresponding curve. This can be carried out automatically by a control unit in device 99, i.e. without the intervention of a doctor. This occurs in preparation for the expected fracture of the occlusion, i.e. when the occlusion dissolves and the suction needle becomes free again—i.e. at the end of the occlusion bar shown. Then, due to the increased aspiration negative pressure, the aspirated liquid quantity is briefly increased-which could lead to an (at least slight) collapse of the eye. However, this can be compensated to a large extent by the partial aspect according to the invention of the precautionary, temporary increase in infusion pressure, since more infusion liquid has already been pumped during the occlusion detected (e.g. in the aspiration pressure increase) as a precaution in this case. Thus, when the occlusion is released, there is sufficient liquid in the eye so that collapse (=collapse of the anterior chamber) can be prevented or at least reduced. After loosening the occlusion and returning to the normal state of the aspiration negative pressure, the infusion pressure can also be normalized again.

FIG. 10 shows an exemplary embodiment of an example of a dynamic adjustment of the infusion pressure with which the active infusion according to the invention as the partial aspect according to the invention can be carried out. A diagram is shown in which, by way of example and simplified to the basic principle, the delivery volume F-asp of the aspiration conveyor device and the delivery volume F-inf of the active infusion conveyor device, which is controlled dependent thereon according to the invention, are shown. This dependency is illustrated here in an exemplary manner in such a way that the infusion is controlled as a function of a predetermined aspiration—in the sense of the invention, however, it is also possible to implement embodiments in which the desired infusion is predetermined and the aspiration is controlled as a function of this. In the diagram, the infusion quantity is always slightly larger than the aspiration quantity, since leakage losses are compensated when the eye is opened. The shown dependence on infusion and aspiration is preferably used as a kind of pilot control, which can additionally be superimposed by a regulation of the actual infusion pressure.

The regulation is thus simplified and can be formed more dynamically, since the control deviation to be compensated is only small. In addition, with a significantly longer time constant, the pilot control can also be slowly adjusted according to the actual leakage loss if necessary and adapted to the actual losses occurring during the specific operation. For example, at the beginning of the intervention the pilot control can be carried out with a leakage rate compensation of 7%, for example, which is usual for this intervention according to experience, which percentage is then e.g. adjusted to 5%, if the superimposed regulation causes a continuous reduction of the infusion quantity over a longer period of time—the intervention opening is thus tighter than usually assumed.

In the upper part of the diagram, the infusion pressure P-sens at the pressure sensor in the cassette, corresponding to the infusion flow rates F-inf and adapted according to the invention, is also shown. The shown increase of the infusion pressure P-sens in the cassette, which is carried out according to this aspect of the invention depending on an increase of the flow rate F-inf, in particular an increased pressure drop in the line to the patient due to flow velocity is compensated for and results in a more balanced, more constant infusion pressure P-inf in the eye than in the prior art. Parameters for this flow rate-dependent target infusion pressure adjustment, e.g. the curve of the adjustment P-sens, can be determined, stored and provided experimentally or computationally for a tube set used in each case.

In the prior art, without active infusion, the above-mentioned advantageous further developments cannot even be taken into consideration, since such prior art systems reacting with inertia cannot be implemented. In addition, the problems which these advantageous further developments solve are not even known in the prior art or are of obvious relevance.

Another prior art problem is that relatively thin tubes are often used for the infusion, and therefore the pressure drop between the BSS bottle and the device cannot be neglected, especially with high infusion flow rates. It also happens frequently that a negative pressure forms in the BSS bottle, which has a negative effect on the infusion pressure in the prior art. A filter in the drip chamber, for example, which causes too much pressure drop, also has a negative effect. In these cases, gravity infusion results in less pressure in the eye and thus less stability.

With the active infusion according to the invention all this does not play a role, since the above problems do not, or at least hardly, affect the infusion pressure in the eye, or are actively compensated by the active infusion.

In particular, pressure measurement on the patient side of the liquid delivery device together with pressure regulation via a peristaltic pump can compensate for the pressure losses mentioned above. In addition, the peristaltic pump can also have a suction effect from the direction of the BSS bottle, which means that the flow rate can be compensated even with high pressure drops in the line, drip chamber, infusion bottle, etc. According to the invention-if necessary-higher flow rates from the BSS bottle can also be achieved than with just a gravity infusion, which can be very helpful in some surgical situations. In particular, it is possible to react quickly and dynamically to any changes, which makes the operation safer. In particular, according to the invention, such a fast and dynamic reaction to possible disturbances can be carried out automatically by the device, i.e. without or with only minor intervention by the personnel, especially via a controller module for the control of the infusion liquid delivery device, which automatically maintains or runs down predetermined target values and/or target value profiles of the infusion pressure on the basis of the sensor technology of the interchangeable cassette.

According to the invention, the infusion pressure measurement is thus arranged in the device, especially in the interchangeable cassette, especially in the flow direction of the infusion after the infusion conveyor device and before the infusion connection of the interchangeable cassette. In accordance with the invention, the control of the infusion—or the regulation of the infusion pressure at the remote surgical instrument connected via the line—is carried out exclusively via the control of a motor drive of the infusion conveyor device, which provides a volume conveying with a defined, known delivery volume. According to the invention, only one pressure sensor in the change cassette is required, since pressure drops are compensated via the line on the basis of the known delivery volume and the resulting flow rate or the flow velocity of the infusion medium through the line. Therefore, no special handpiece or surgical instrument is required for the infusion according to the invention, and in particular only a fluidic and no electrical connection. In addition, according to the invention, for example when an occlusion in the aspiration path is detected by an aspiration pressure sensor attached to the aspiration path, a pressure change in the infusion can occur which is especially dependent on the aspiration and which is especially also preventive. According to the invention, a leak rate compensation of the known infusion volume in comparison to a known aspiration volume can also be formed, for example by controlling the infusion conveyor device with a defined higher known delivery volume than that of an aspiration conveyor device and/or always providing a defined minimum delivery volume of the infusion.

In other words, one embodiment of the invention relates to a method with remote sensing pressure regulation at an infusion point connected to a conveyor device via a line, in which a pressure drop in the line is determined depending on a delivery volume of the infusion medium and a target value for a pressure of the infusion medium at the conveyor device is adjusted accordingly. In particular, this can be carried out, for example, by detecting a pressure of the infusion medium by means of a pressure sensor in the device arranged between the peristaltic pump and a connection to the line, and increasing a target value of the pressure as a function of the delivery volume to compensate for a pressure drop in the line, especially when these methods are provided in an ophthalmological device.

In other words, in an ophthalmological device an infusion pressure at the end of an infusion tube—i.e. the eye—can be determined according to the invention by knowing a pressure in the device and a flow volume for a known infusion tube. In comparison with pressure measurement directly on the eye for example, this is not only easier to install and less prone to errors but also results in an advantageous pressure regulation behavior for this specific application.

The invention claimed is:

1. An ophthalmological device which provides suction flushing with an aspiration function and an infusion function, comprising:
   one or more connectors configured to couple with a surgical instrument outside the ophthalmological device;

an aspiration conveyor device for motor-driven discharge of liquid from the surgical instrument into a waste container, based on peristaltic pumping or vacuum suction;

an infusion conveyor device for motor-driven feeding of an infusion medium from an infusion container via an infusion connection and a line to the surgical instrument, wherein the infusion conveyor device is designed as a peristaltic pump for active infusion volume delivery of the infusion medium with a known delivery volume to the surgical instrument;

a pressure measuring device with a pressure or force sensor in the ophthalmological device, wherein the pressure measuring device is formed between the infusion conveyor device and the surgical instrument, and is configured to determine an infusion pressure of the infusion medium in the ophthalmological device;

an interchangeable cassette removably disposed in the ophthalmological device, wherein regions of the infusion conveyor device that come into contact with the infusion medium together with regions of the aspiration conveyor device that come into contact with the liquid are formed in the interchangeable cassette; and a controller configured to regulate the infusion volume delivery based on the infusion pressure and a pressure drop in the line to the surgical instrument, wherein the pressure drop in the line to the surgical instrument is at least partially compensated with a pressure increase in the infusion volume delivery, wherein the pressure measuring device comprises a flexible membrane in the interchangeable cassette, and wherein the pressure or force sensor is disposed outside the interchangeable cassette and in contact with the flexible membrane.

2. The ophthalmological device according to claim 1, wherein the pressure drop is determined by taking into account a flow velocity of the infusion medium, wherein the flow velocity is determined based on a current delivery volume of the infusion volume delivery.

3. The ophthalmological device according to claim 1, further comprising:
an infusion drive for the infusion conveyor device and an aspiration drive are separate from the interchangeable cassette for the aspiration conveyor device.

4. The ophthalmological device according to claim 1, wherein the controller is configured to adjust a deliver rate of the infusion conveyor device based on a target value of the infusion pressure.

5. The ophthalmological device according to claim 1, further comprising:
a motor-driven height adjustment device configured to adjust a height of the infusion container; and
a bypass valve device configured to switch between a first operation that the infusion medium engaging the infusion conveyor device and a second operation that the infusion medium bypassing the infusion conveyor device.

6. The ophthalmological device according to claim 5, wherein
the first operation corresponds to providing a first hydrostatically pressure-adjustable infusion based on the motor-driven height adjustment device adjusting the height of the infusion container, and
the second operation corresponds to providing a second pressure-adjustable infusion based on operating the infusion conveyor device.

7. The ophthalmological device according to claim 1, wherein the aspiration conveyor device and the infusion conveyor device are constructed in a similar manner in their design and dimensioning.

8. The ophthalmological device according to claim 1,
wherein the interchangeable cassette comprises a flexible line region between the infusion conveyor device and the surgical instrument, the flexible line region being configured to effect a compensation of fluctuations in a delivery volume of the infusion conveyor device based on passive ripple compensation caused by elastic deformation of the flexible line region, and/or
wherein an air bubble sensor is formed along a path of the interchangeable cassette in which the infusion medium is supplied, the air bubble sensor including a viewing window in the interchangeable cassette and an optical monitoring system outside the interchangeable cassette.

9. The ophthalmological device according to claim 1, wherein the infusion conveyor device comprises:
in the interchangeable cassette, at least one squeezing channel, which is formed at least approximately in a circular arc and is made of an elastic material; and
one or more actuators including rollers disposed outside the interchangeable cassette, the one or more actuators are configured to squeeze the at least one squeezing channel to cause formation of at least one squeezed portion and at least one unsqueezed portion of the at least one squeezing channel and to move the at least one squeezed portion and the at least one unsqueezed portion along the at least one squeezing channel,
wherein, based on the at least one squeezing channel including a plurality of squeezing channels, the squeezing channels are arranged hydraulically parallel and actuated phase-shifted with respect to one another.

10. The ophthalmological device according to claim 8, wherein the ophthalmological device comprises the air bubble sensor, and the viewing window is disposed between the infusion connection and the infusion conveyor device.

11. The ophthalmological device according to claim 1, further comprising:
a second pressure measuring device with a second pressure or force sensor in the ophthalmological device, wherein the second pressure measuring device is formed between the aspiration conveyor device and the surgical instrument, and is configured to determine an aspiration pressure of the liquid from the surgical instrument,
wherein the controller is configured to detect occlusion of an aspiration based on the aspiration pressure and to increase the infusion volume delivery based on the detected occlusion.

* * * * *